United States Patent [19]
Grim et al.

[11] Patent Number: 5,761,834
[45] Date of Patent: *Jun. 9, 1998

[54] FOOTGEAR WITH PRESSURE RELIEF ZONES

[75] Inventors: Tracy E. Grim, Broken Arrow, Okla.; Kevin Richard O'Donnell, Thousand Oaks; Eric Gerard Montag, Van Nuys, both of Calif.

[73] Assignee: Royce Medical Company, Camarillo, Calif.

[*] Notice: The portion of the term of this patent subsequent to Feb. 16, 2013, has been disclaimed.

[21] Appl. No.: 360,798

[22] PCT Filed: Feb. 16, 1994

[86] PCT No.: PCT/US94/01797

§ 371 Date: Jan. 6, 1995

§ 102(e) Date: Jan. 6, 1995

[87] PCT Pub. No.: WO94/18863

PCT Pub. Date: Sep. 1, 1994

Related U.S. Application Data

[63] Continuation-in-part of Ser. No. 17,818, Feb. 16, 1993, Pat. No. 5,329,705.

[51] Int. Cl.⁶ .............. A43B 13/38; A61F 5/00; A61F 5/37
[52] U.S. Cl. .............. 36/88; 36/93; 36/95; 36/110
[58] Field of Search ................ 36/43, 44, 71, 36/88, 95, 93, 110, 140, 155; 602/23

[56] References Cited

U.S. PATENT DOCUMENTS

| 975,576 | 11/1910 | Sexton | 36/140 |
| 2,885,797 | 5/1959 | Chrencik | 36/91 |
| 2,909,854 | 10/1959 | Edelstein | 36/140 |
| 2,913,837 | 11/1959 | Geuder | 36/71 |
| 2,979,836 | 4/1961 | Scholl | 36/44 |
| 3,548,420 | 12/1970 | Spence | 36/71 |
| 3,859,740 | 1/1975 | Kemp | 36/71 |
| 4,100,686 | 7/1978 | Sparlato et al. | 36/29 |
| 4,408,402 | 10/1983 | Looney | 36/43 |
| 4,571,853 | 2/1986 | Medrano | 36/29 |
| 4,689,898 | 9/1987 | Fahey | 36/43 |
| 4,793,078 | 12/1988 | Andrews | 36/43 |
| 4,869,001 | 9/1989 | Brown . | |
| 4,893,418 | 1/1990 | Ogden . | |
| 5,078,128 | 1/1992 | Grim et al. | 602/23 |
| 5,154,682 | 10/1992 | Kellerman | 36/44 |
| 5,197,942 | 3/1993 | Brady | 602/23 |
| 5,329,705 | 7/1994 | Grim et al. | 36/88 |

*Primary Examiner*—M. D. Patterson
*Attorney, Agent, or Firm*—Oppenheimer Poms Smith

[57] ABSTRACT

Footgear with an inner sole (66) having a grid of removable resilient elements to permit removal of selected elements (68) to provide relief to ulcerated or injured areas of the foot. An air bladder (64) may underlie sole (66), preferably with additional cushioning material (40) within the air bladder. A walker (12) with a soft support (20) may be provided with the inner sole within the support. Some of the removal resilient elements may have a higher density or height than others. The footgear may include an adhesively-backed resilient pad (212) to provide additional support to a region. The footgear may include means for reducing shear stress on a bottom surface of the foot. An edema patch (240) may be provided for covering an open space (248) left after a user has removed a removable section from the grid. The edema patch applies pressure to the afflicted zone of the foot (250) preventing fluids from building up.

23 Claims, 11 Drawing Sheets

FOOTGEAR WITH PRESSURE RELIEF ZONES

RELATED PATENT APPLICATIONS

This application is a continuation-in-part of U.S. patent application Ser. No. 08/017,818, which was filed Feb. 16, 1993 now U.S. Pat. No. 5,329,705. This invention is related to that disclosed in U.S. patent application Ser. No. 07/965,750, filed Oct. 23, 1992, (Docket No. 88-182), entitled "Orthopaedic Support and Method for Providing Semi-Permanent Relief Zones," assigned to the assignee of this invention.

FIELD OF THE INVENTION

This invention relates to footgear having orthopaedic soles providing pressure relief areas for the feet.

BACKGROUND OF THE INVENTION

The problems solved by the present invention were discussed at length in the prior patent application cited above, and the background section of that application will therefore be repeated here.

Support pads are used in a wide variety of applications to provide cushioned support to an injured or otherwise sensitive bodily appendage. Such pads have the dual purpose of (1) providing orthopaedic support to the appendage and (2) protecting the appendage from further injury or damage resulting from contact with a foreign object or hard surface.

One common use of a support pad is as a cushioned foot sole in specialized footwear such as soft boots or patient walkers. These devices generally employ some type of soft, resilient material, such as foam, to provide cushioned support of a sensitive or damaged foot.

A particular problem arises when it becomes necessary to provide uneven support across the outer surface of an appendage. For example, an ulcerated appendage, often found in diabetic patients, requires pressure relief to the ulcerated area to allow healing. In this instance, it is desirable to have a pad which will apply cushioned support to the appendage, while refraining from supporting the afflicted area. For diabetic patients, the feet are commonly beset with such ulcerations, and it is therefore desirable to provide a cushioned support sole for a shoe or walker which is capable of providing specific zones of pressure relief.

Other approaches have addressed the problem of providing cushioned foot support. U.S. Pat. No. 2,598,217 (Bronson), issued May 27, 1952, discloses an invalid's boot with a thick insole. However, these approaches require replacement of the sole for each new patient, or for each new area of the original patient's foot which must be relieved.

Andrews U.S. Pat. No. 4,793,078 discloses a footwear insole with a molded arch support. The insole has either three indentations or a single banana-shaped indentation arranged in an arc behind the toes, and another indentation at the heel. A user may adhesively fix pad inserts into one or more of the indentations to provide support to the foot. The user omits inserts from selected indentations to relieve pressure on certain areas of the foot.

Unfortunately, a number of problems arise when diabetes patients, who are prone to severe foot ulcers, attempt to use the Andrews device. Before discussing these deficiencies, however, it is useful to review the foot problem that many diabetes patients face. It is well known that diabetes patients are prone to foot ulcers. In fact, lesions of the foot are responsible for more than one-fifth of the hospitalizations of diabetic patients. More than 40% of the lower extremity amputations in the United States are performed on diabetic patients who have poor circulation in the lower limb. With reduced sensation in the foot, the patient is unlikely to feel discomfort when the skin is subject to shear forces during walking, and consequently he or she does not properly adjust his or her gait. Lesions are formed or are made worse.

Diabetes patients also experience other extreme difficulties with their feet. Diabetic patients often undergo an unfortunate evolutionary pattern of anatomical deterioration. Initially, the foot will have a normal appearance and will only have vascular or neuro-vascular deficiencies. However, the bone structure can quickly deteriorate. Charcot joints can form, and the foot becomes drastically deformed. From then on, the areas of the foot that can bear weight are abnormal, their locations are unpredictable, and custom foot accommodations will be required for the remainder of the person's ambulatory life.

The Andrews device does little to overcome these problems. Foot ulcers and bone deterioration can occur anywhere on the foot, yet Andrews provides only a few pads in very specific locations. The Andrews fixed-location pad arrangement cannot provide pressure relief to damaged areas of the foot that are located anywhere except the four specific pad locations. This makes Andrews inadequate for the majority of diabetes patients with damaged feet.

An additional drawback of the Andrews pad is that it lacks means to reduce shear forces on the skin of the foot that arise as the patient walks along. Such shear forces can further damage existing ulcers, or create new ulcers. This is particularly true where the patient walks for any distance.

Other deficiencies of Andrews are apparent. As shown in Andrews FIG. 1, the Andrews sole is limited to either a left or right foot-only sole. The same Andrews sole cannot be used on either foot because sole support 16 is built into the shoe.

U.S. Pat. No. 3,760,056 (Rudy), teaches a method for conforming a ski boot to the foot of the wearer by heating an inflatable bladder, distending it to the desired shape, and then cooling and deflating the bladder. The bladder can be subsequently be re-inflated to fit the wearer's foot. This method requires a mechanism for heating, which may be inconvenient or impractical when applied to a conformable sole. In the method disclosed, the inflatable bladder was placed over the foot to contact opposing sides, rather than underneath it as a support. Moreover, the elastomeric materials described in the Rudy patent typically may not provide the requisite comfort and cushioning generally required in a healing device.

A further method of providing support to an injured foot is disclosed in U.S. Pat. No. 5,078,128 (Grim, et al.) in which a removable leg walker includes a plurality of inflatable and adjustable bladder members in order to provide variable amounts of pressure to an affected limb as leg swelling increases or decreases. However, the bladder members of the Grim device do not retain their shape except as restrained by the surface of the appendage itself and thus do not provide the desired semi-permanent areas of relief to an injured appendage.

Incidentally, the above-cited U.S. patent application Ser. No. 07/965,750 discloses arrangements which provide relief using a pad of particulate material which is vacuum formed to the desired configuration.

From an overall standpoint, a principal object of the present invention is to provide a comfortable cushioned sole which may be conveniently modified to provide pressure relief to specific areas of the wearer's foot.

Another important object of the invention is to furnish a device which may be reused to provide relief to different areas of the patient's foot, or which may be used by other patients.

A further object is to provide a method for conforming a cushioned sole to the foot of a particular wearer, and of later reforming or returning the sole to its original shape.

SUMMARY OF THE INVENTION

In accordance with one illustrative embodiment of the invention, a walker frame, including an outer sole and side struts may be provided with an air bladder mounted above the outer sole, and a special inner sole mounted above the bladder and made up of a large number of separate resilient sections removably secured to a flexible sheet to form a substantially flat surface for engagement by the foot. In areas where the foot is ulcerated or otherwise injured, sections of the inner sole are removed to provide pressure relief.

In accordance with a broader aspect of the invention, footgear or footwear generally may be provided with an inner sole having mobile sections of the type described in the preceding paragraph.

With regard to the walker embodiment, a flexible soft goods-type support may be provided, to enclose the patient's foot, and having arrangements for securing to the walker frame. The bladder may be mounted between the outer sole and support, layered within the soft goods support, or preferably above the soft goods support. A dorsum strap may be secured to the support or the inner sole and extend around the ankle and instep, to hold the foot in place on the inner sole.

Additional features of the invention may include the following:

1. The removable sections may be held in place by pressure sensitive adhesive or preferably hook and loop type securing material of the Velcro type to permit removal and replacement of the sections.
2. The removable sections may be in a grid like configuration, using hexagonal, rectangular or square patterns.
3. The inner sole may have multiple layers, with the layer closest to the foot being softer and more resilient than other layers.
4. The inner sole may extend to the rear and upward to cushion the rear of the heel.
5. The bladder may be filled with fluid, air, other gas, liquid, or gel material.
6. The bladder may contain additional resilient material such as a layer of foam, for extra cushioning of the foot.
7. The removable sections can be arranged on a substantially indentation-free surface.
8. The removable sections may cover most or substantially all of the inner sole, or may cover selected important areas such as the heel and ball of the feet areas.
9. The removable sections may have various densities so that a user may arrange denser sections to provide additional cushioning in selected areas of the inner sole.
10. The removable sections may have various heights so that a user may arrange the sections to custom-fit the foot.
11. An edema patch may be provided for covering an open space left after a user has removed one or more mobile sections from the grid and for applying pressure to the afflicted zone of the foot, thereby preventing fluids from building up in the afflicted zone of the foot.

Other objects, features and advantages of the invention will become apparent from the following detailed description and from the accompanying drawings.

DETAILED DESCRIPTION OF THE PREFERRED EMBODIMENTS

Figure 1:
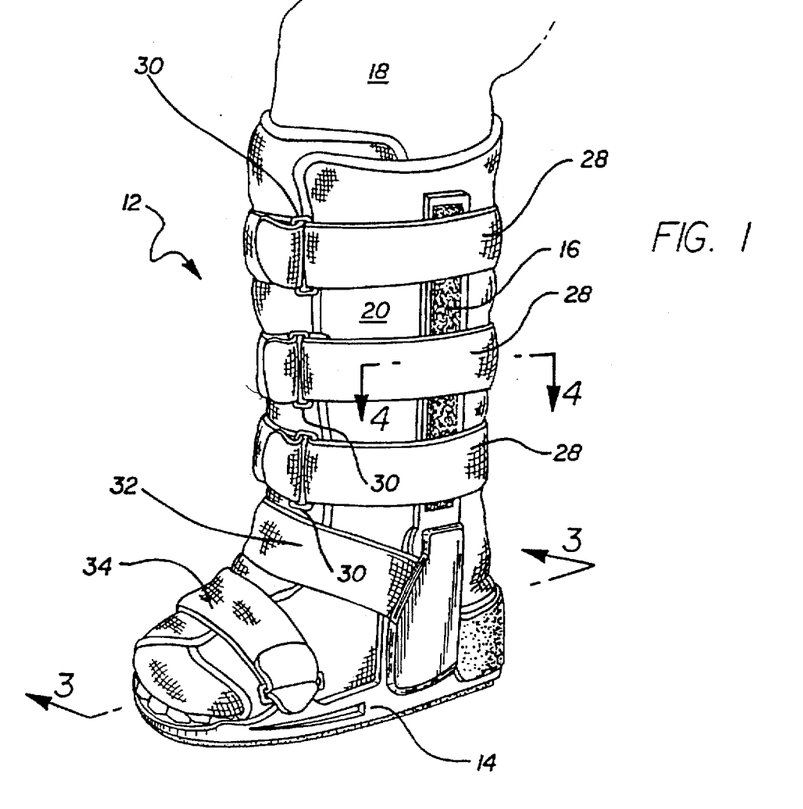
FIG. 1 is a perspective view of a walker of the type to which the present invention is applicable.
Figure 4:
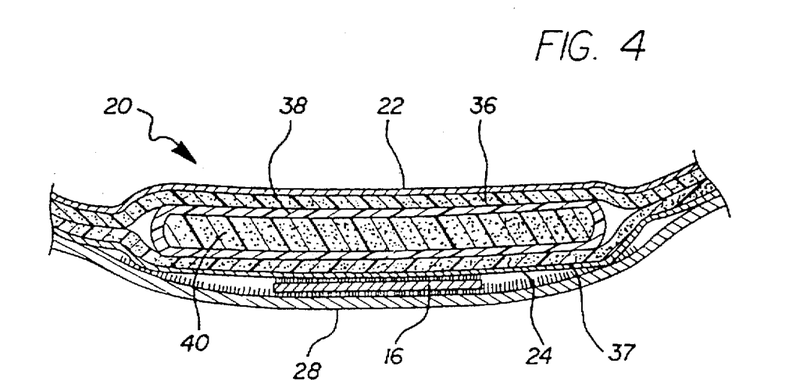
FIG. 4 is a cross-sectional view taken along lines 4—4 of FIG. 1.

Referring more particularly to the drawings, FIG. 1 shows a walker 12 including a frame made up of an outer sole assembly 14 and two side struts 16 secured to the sole, and extending up on either side of the lower leg of the patient 18. Within the frame 14, 16, is a soft goods type support member 20 for enclosing the lower leg, ankle and most of the foot of the patient or user. As best shown in FIG. 4, the soft goods type body member 20 includes outer cloth material 22 and 24 separated by two layers of foam 36 and 37, which may be either foam rubber or foamed urethane, by way of examples. The soft goods type body member 20 may be held in position within the frame 14, 16, by pads of hook and loop type material on the inner surface of the struts 16, and by the straps 28 extending around the struts 16, through the D-rings 30 and then being folded back on the other portions of the straps, and held in adjustable positions by mating Velcro type hoop and loop areas on the surfaces of the straps. The straps 32 and 34 across the instep and the forward portion of the assembly, operate in similar manners to hold the foot and the soft goods type support member 20 in position within the frame 14, 16.

Incidentally, with regard to the detailed construction of the walker frame, reference is made to U.S. Pat. No. 5,078,128, granted Jan. 7, 1992, and assigned to the assignee of the present invention.

One of the straps 28 is also visible in FIG. 4 as is one of the struts 16. Between the body member 20 and the strut 16, and between the strut 16 and the strap 28, is hook and loop type material, so that various members are secured in place relative to one another.

Within the side walls of the soft goods body member 20, may be air bladders such as that shown at reference numeral 38 in FIG. 4 and preferably containing a layer of open cell foam 40. The bladder 38 may be located between one layer of foam 36 and fabric 22 and the second layer of foam 37 and fabric 24. This arrangement provides additional cushioning for the lower leg of the patient, particularly in the vicinity of the struts 16.

Figure 2:
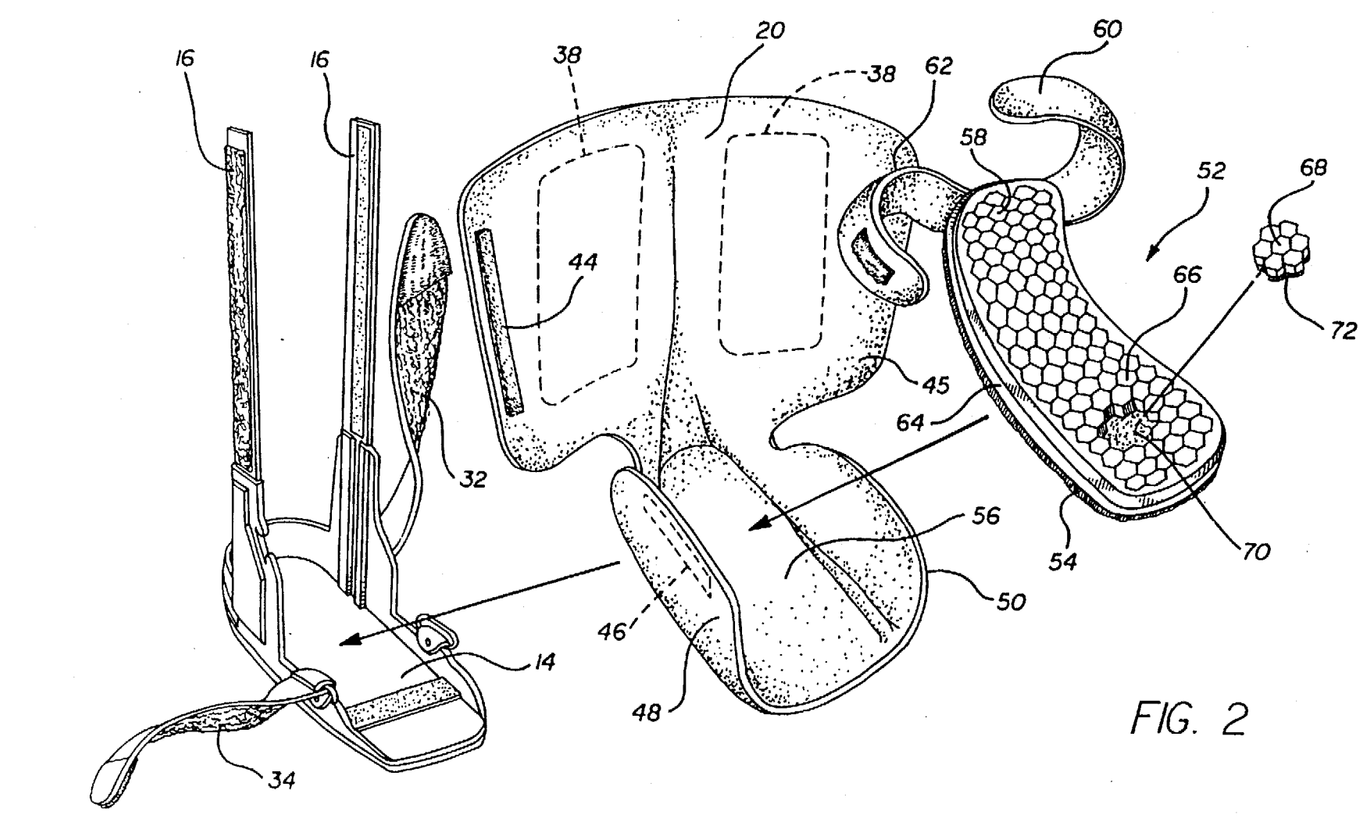
FIG. 2 is a partial exploded view of the walker of FIG. 1.

FIG. 2 is a partial exploded view of the walker of FIG. 1, with reference numerals employed in FIG. 1 being carried over to FIG. 2. Shown in FIG. 2 is the elongated pad 44 of hook type material. The outer cloth covering of the soft goods type body member 20 is of cloth of one of the well known types such as brushed nylor material which will receive hook type securing pads, such as that sold under the trademark "Velcro" so that the front upper portion of the soft goods type support member 20 may be held in the closed position by the engagement of the pad 44 with the outer surface of the mating portion 45 of the support member 20. Similarly, the pad 46 on the inner surface of the front flap 48 of the soft goods support member 20 serves to engage the mating flat 50 on its outer surface, and holds the front portion of the soft goods member around the upper portion of the patient's foot.

The footgear of the present invention is provided with an inner sole assembly 52 which is preferably mounted within the soft goods support member 20 by a layer of hook type securing material 54 which is on the lower surface of the assembly 52, and which engages the inner surface of the soft goods type support member 20 in the area 56 as shown in FIG. 2. The rear portion 58 of the inner sole assembly 56 may extend up behind the heel of the patient to cushion this area of the foot; and the straps 60 and 62, formed of soft material and held together by hook and loop type securing arrangements, served to hold the patient's foot back into proper engagement with the inner sole assembly 52.

Inner sole assembly 52 includes a lower air bladder 64 which may contain a layer of foam material, and an upper resilient layer 66 constituting separate removable sections, also known as individually mobile resilient sections, which together form a normally substantially smooth surface for engagement by the foot. These sections are individually removable, as indicated by the sections 68 which are shown removed from the space 70 where they would normally be located to complete the smooth upper surface of the inner sole assembly 52. The concept, as mentioned in the introductory portion of the present specification, is to provide relief to ulcerated or injured portions of the foot, whereby the foot is supported on the adjacent resilient material, with relief provided in the areas where the removable sections have been taken away.

The top surface of bladder 64 may be substantially indentation-free so that the resilient sections may be removed from any location on the grid. The user is thereby not limited to removing inserts only from indentations located in a limited number of positions on the sole, such as in the Andrews patent discussed in the Background section. Instead, a user of the present invention may remove sections from precisely the desired location.

Note that the individual resilient sections such as the section 68, have hook or loop type securing material 72 on their lower surfaces, and the upper surface of the bladder 64 has mating hook and loop type material for removably securing sections such as section 68 in place to provide a relatively smooth upper surface. Thus, the group of sections 68 may be reinserted and re-secured into the opening 70, and other sections removed, to accommodate different needs, or the problems of another patient. Instead of using hook and loop type securing material as shown in FIG. 2, the lower surface of sections such as the sections 68 may be provided with pressure sensitive adhesive, thereby providing the removable and replaceable functions as discussed hereinabove.

Figure 3:
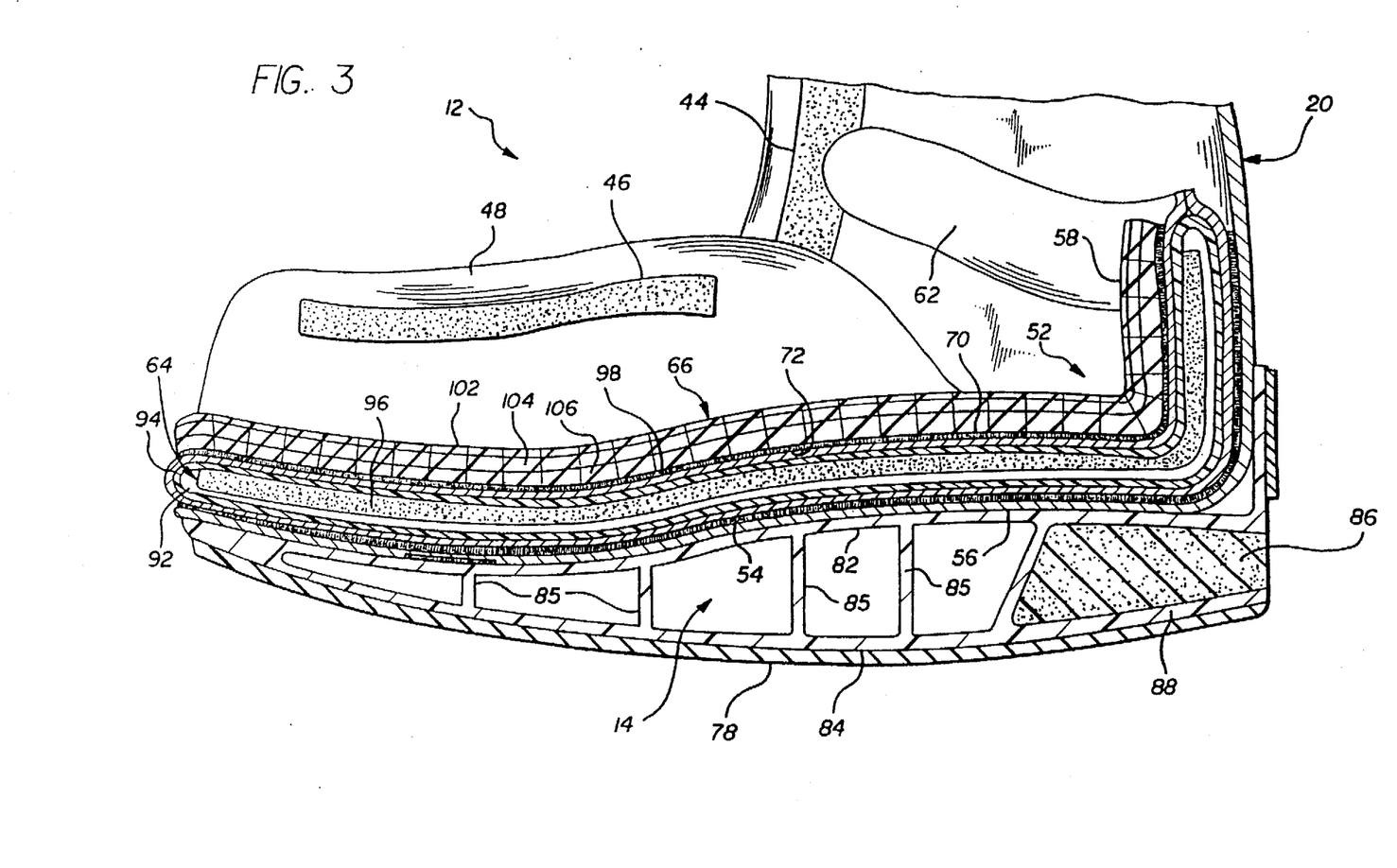
FIG. 3 is a partial cross-sectional view taken along lines 3—3 of FIG. 1.

FIG. 3 is a somewhat schematic cross-sectional view taken along line 3—3 of FIG. 1. More specifically, the view of FIG. 3 includes the soft goods type support member 20 which is here shown as a single layer for simplicity, but which, in reality, would be two layers of cloth and two foam layers forming a central foam core, as discussed in connection with FIG. 4. In addition, FIG. 3 shows the outer sole 14 including the lower tread portion 78, which would normally be somewhat rough for traction, the flap 48, the strap 62, the bladder 64, and the resilient inner sole 66.

Concerning the sole 14, in addition to the outer tread portion 78, it may include the upper and lower high strength plastic sheet members 82 and 84 which are interconnected by appropriate ribs 85. At the rear of the sole 14 is a cantilevered area in which resilient foam material 86 is located, so that controlled flexing of the rear heel end 88 of the lower plastic sheet member 84 provides increased cushioning for the patient, against shock to which he or she might otherwise be subjected.

Regarding the bladder assembly 64, it may include a sealed bladder made of thin sheet urethane 92 covered with cloth material 94, and containing an open cell foam layer 96 which may be bonded to the upper or lower surface of the bladder. Between the upper surface of the bladder assembly 64, and the lower surface of the inner sole 66 is a suitable material 98, for removably securing the inner sole 66 to the upper surface of the bladder 64. Material 98 may be hook and loop type material, or pressure sensitive adhesive, as noted hereinabove. The inner sole 66 may be formed of three layers 102, 104 and 106, which are bonded together. These three layers 102, 104 and 106 may be of progressively different softness and resiliency, with the softest and most resilient layer being the layer 102 closest to the foot, with layers 104 and 106 being progressively less resilient and providing somewhat greater support.

It should be noted that bladder 64 is entirely optional. Inner sole assembly 52 may alternatively include a flexible pad rather than bladder 64. The flexible pad may be made of a material such as cloth with which a hook and loop type material can engage.

With regard to the construction of the outer sole assembly 14, it may be formed as described hereinabove in the cited U.S. Pat. No. 5,078,128, or may be of any other desired configuration. The present invention is primarily directed to a configuration of the inner sole, and the precise configuration of the outer sole arrangements may be chosen from many alternatives.

Figure 5:
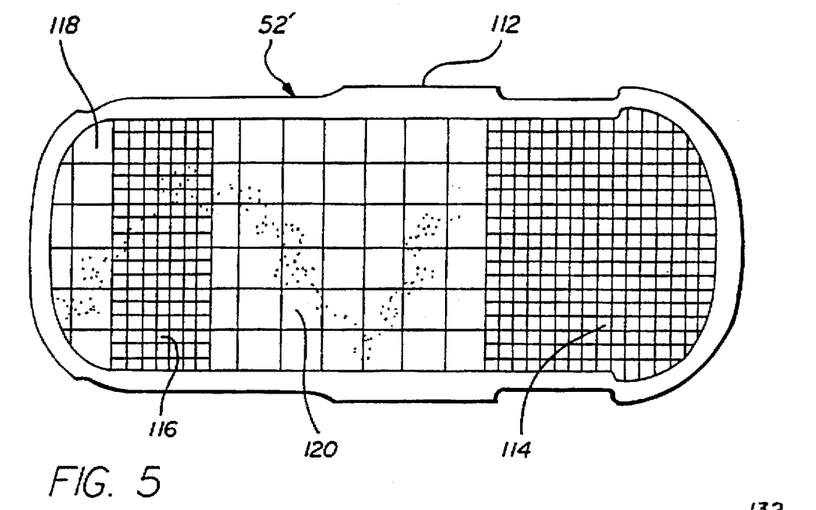
FIG. 5 is a top view of an alternative inner sole configuration.

FIG. 5 shows an alternative arrangement of the individual removable sections of the inner sole which is designated by the reference numeral 52'. In addition to the continuous outer rim 112, the sections are rectangular, or square, and have a closer spacing in the heel area 114, and in the area 116 immediately behind the toes. The area 118 where the toes would be located, and the central area 120 below the instep, could have larger sections, as these areas are less likely to have ulcerations and require relief. It is noted in passing, however, that the hexagonal configuration as shown in FIG. 2, is the presently preferred embodiment.

Figure 6:
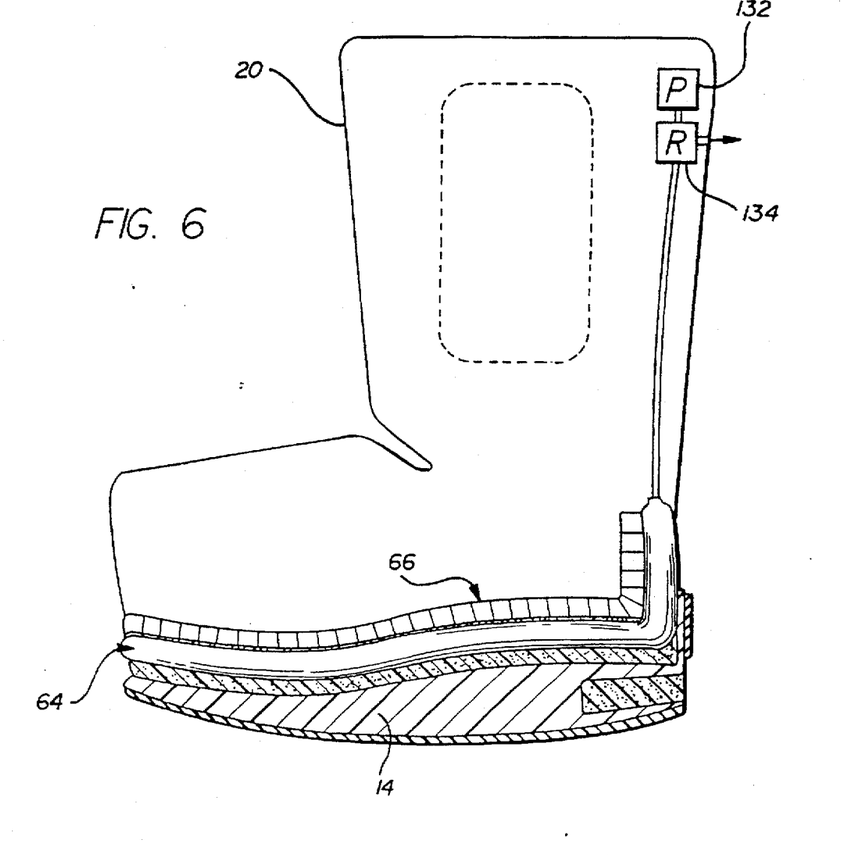
FIG. 6 is a schematic showing of a walker system implementing the principles of the invention.

Regarding FIG. 6, this is a schematic showing of a walker illustrating the principles of the invention and shows the soft goods type support 20, the sole 14, the bladder 64, and the inner sole 66. The bladder 64 may be a sealed bladder, preinflated, or may be provided with a pump 132, and pressure relief arrangements 134. The pump 132 may be manually actuated, mechanically actuated, or may be actuated by a walking or running action of the user. The pressure relief arrangements 134 may involve a simple adjustable spring and ball type controlled pressure relief valve, or may involve more complex pressure sensing and valve actuation arrangements controlled by the sensing of the pressure.

Regarding FIGS. 7–11, one alternate embodiment of the present invention employs separate removable resilient sections having different material densities. Some of the resilient sections are lower density sections and some are higher density sections, so that a user may arrange the higher density sections to create at least one zone of additional support for a foot. The zone or zones of higher density sections serve to selectively absorb energy during portions of the walking gait.

For instance, concentrating resilient sections made of dense material in the midfoot region will help distribute force throughout the surface of the plantar pad during the gait. As with the other embodiments of the present invention, the removable resilient sections are arranged in a grid. The user removes selected resilient sections in order to create a customized pressure relief zone of desired location and dimensions.

Dense material may also be added to specific regions of the foot to absorb energy where needed, such as the heel region or the instep region. These areas may experience high stress and therefore require additional padding.

Alternatively, the midfoot region of the plantar pad may be of a denser material than the heel or the forefoot region. Body weight then shifts onto the middle foot area and off of the front and heel portions of the foot. In other words, during the gait the denser material will support the midfoot region, while the heel and forefoot sink into the less dense material. It should be emphasized, however, that the less dense material must be sufficiently dense so as to prevent the foot from hitting the bottom of the pad, which is known as "bottoming out".

There are at least two other uses for resilient sections having increased density. First, dense resilient sections may be arranged around the perimeter of a pressure-relief area where resilient sections have been removed. The denser sections provide additional support, and serve to prevent the ulcerated area of the foot from bottoming out in the unsupported area.

Second, dense resilient sections may be used to prevent "compression set", which is a permanent reduction in cross-section arising from constantly stepping down on the material. A denser material is stronger and more durable, and is less likely to become permanently deformed than a less dense material. Consequently, use of resilient sections having increased density can result in increased durability and product life.

Figures 7, 8, 9, 10, 12:
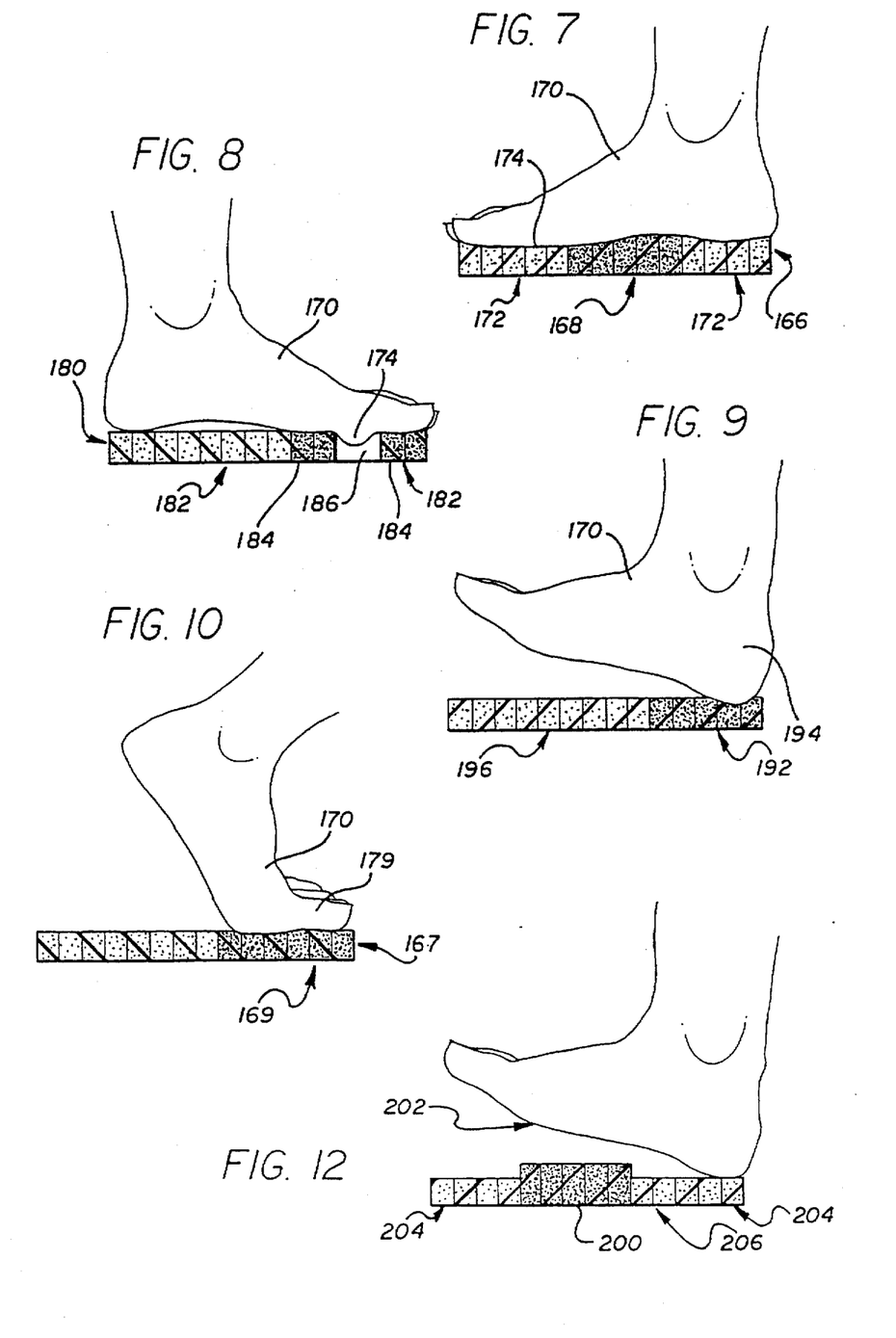
FIG. 7 is a side view of a support pad which has dense removable sections arranged underneath the arch of a user's foot.
FIG. 8 is a side view of a support pad which has dense removable sections arranged around a pressure relief area from which sections have been removed.
FIG. 9 is a side view of a support pad which has dense removable sections arranged in the heel area to absorb impact as a user steps down on the pad.
FIG. 10 is a side view of a support pad which has dense removable sections arranged in the ball region of the foot to absorb the pressure of stepping forward.
FIG. 12 is side view of a pad having taller removable members arranged underneath the arch of a foot.

FIGS. 7–11 illustrate some of the various ways that a user or physician might arrange resilient sections of different densities on the pad. FIG. 7 illustrates an inner sole 166, also known as a plantar pad, having removable resilient sections of different densities. A region 168 of high-density removable sections supports the arch section of foot 170. As the user steps down on plantar pad 166, high density region 168 reduces the load that lower density regions 172 would otherwise carry. Consequently, high density region 168 reduces pressure from ulcerated area 174 of foot 170.

FIG. 8 illustrates an alternative distribution of high density removable sections on an inner sole or plantar pad 180. Most of the surface area of plantar pad 180 is covered with normal density removable pads 182. However, higher density removable pads 184 surround pressure relief area 186 where pads have been removed. These dense pads 184 provide additional support in the area immediately adjacent to ulcerated area 174. In particular, these dense pads serve to reduce the chance that ulcerated area 174 will "bottom out" or displace vertically below the bottom of pad 180 during walking and running, which would impact ulcerated area 174 and potentially further injure the foot.

FIG. 9 shows that dense sections 192 are arranged in a rear portion of plantar pad 190. These dense sections 192 can absorb shock better than normal density pads 196 and, in this instance, help compensate for the "heel strike" that occurs as the user steps down onto heel 194 of the foot 170. It should be noted that many diabetic patients are obese, and that the heel may be subjected to significant loading while the user walks around. The arrangement of dense sections 192 of FIG. 9 reduces the risk of heel injury from such significant heel loading.

FIG. 10 shows that dense sections 169 may be arranged in a front portion of a plantar pad 167 in the area of the ball and toes of foot 170. This arrangement of dense sections 169 provides support during the "push-off" part of the walk when the person pushes hard against the forward portion of the foot to move the body forward. Dense sections 169 absorb this "push-off" pressure, and protect the ball and toes 179 of foot 170 from bottoming out against a support layer below plantar pad 167.

Figure 11:
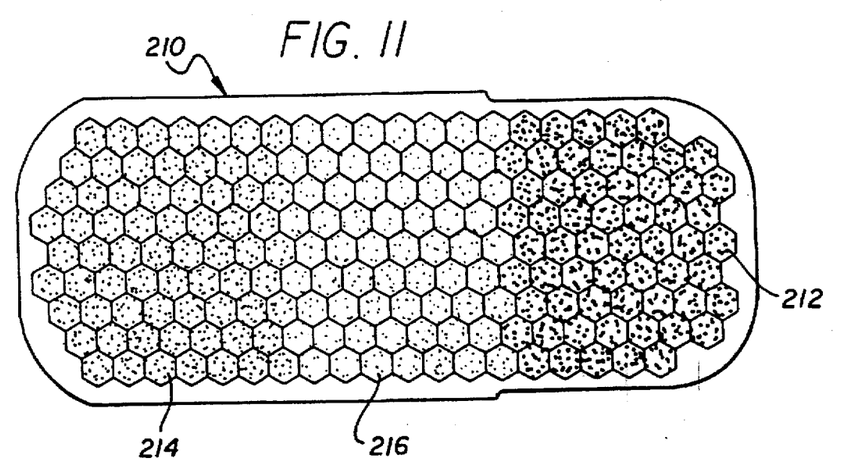
FIG. 11 is a top view showing a support pad having high density removable sections in the toe area, and less dense removable sections in the mid-foot region.

FIG. 11 illustrates a plantar pad 210 having three different densities of removable resilient pads. High density pads 212 are arranged in the heel area of the plantar pad. These pads compensate for the significant shock loading of heel strike. Medium density pads 214 are arranged to correspond to the toe and ball area of the foot to provide support during pushoff loading. Lower density pads 216 support the rest of the foot.

Figure 13:
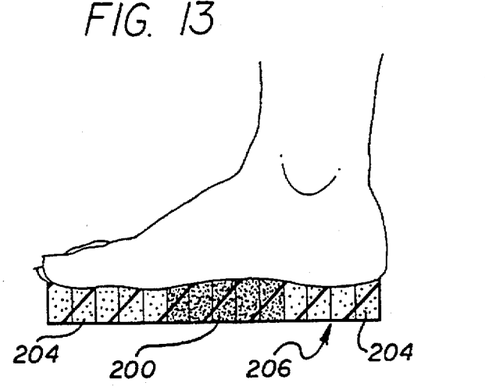
FIG. 13 is a side view showing that the members of the pad of FIG. 10 custom-fit the countour of the foot when the user is standing on the pad.

Another alternative embodiment uses some separate resilient sections that are taller than other sections. A user may arrange the taller sections to custom fit a foot. FIG. 12 shows that tall removable sections 200 have been arranged underneath the arch of a user's foot 202. Regular height sections 204 support the other areas of the foot. When the user steps onto the pad 206 as in FIG. 13, the taller sections 200 fully support the arch of the foot. In addition, the taller sections 200 carry more of the user's body weight than would regular-height sections.

Figure 14:
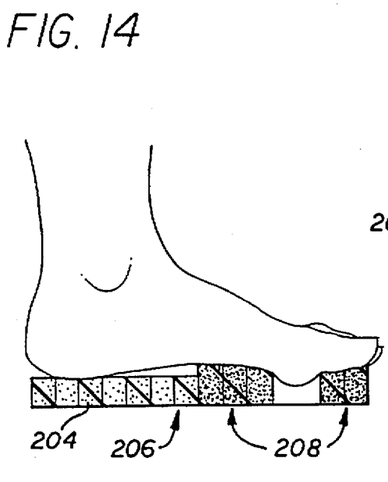
FIG. 14 is a side view of a pad having taller members arranged around a pressure relief zone from which removable members have been removed.

Taller sections can be arranged around an area of pressure relief, as in FIG. 14. This region of taller sections 208 serves two purposes. First, the taller sections raise the foot in the region of the pressure relief area, thereby reducing the chances that the injured area will "bottom out" against the bottom of the pad when the user steps down on the foot. Second, the taller sections carry more weight around the pressure relief area than would shorter sections. Consequently, the region of tall sections 208 of FIG. 14 provides greater pressure relief to the injured area. It should be noted that the taller sections 200 in FIG. 12 may be rearranged to form the configuration of the pad in FIG. 14.

As noted above, a heavy patient or a patient with a particularly large ulcer may "bottom out" the afflicted area against the bottom of the pad during walking. To prevent "bottoming out", the user may apply an additional resilient pad having an aperture and an adhesively-backed lower surface. The lower surface adheres to the upper surface of resilient sections surrounding a pressure relief zone. The additional pad provides extra support around the pressure relief area.

Figure 15:
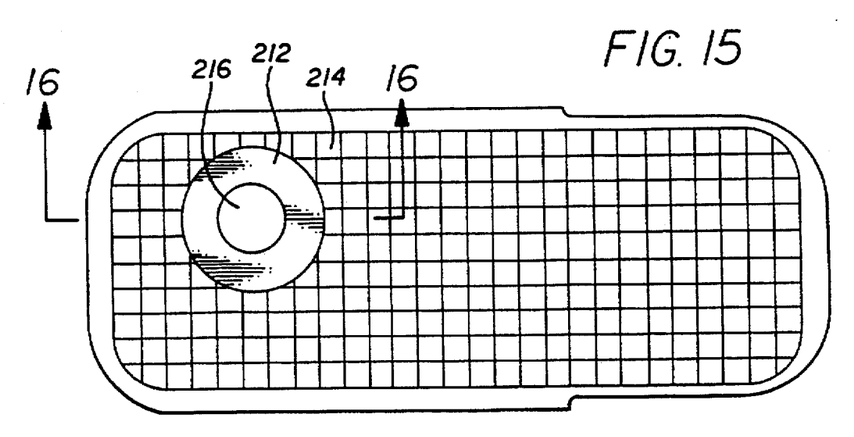
FIG. 15 is a top view showing an additional pad applied on top of removable members.
Figure 16:
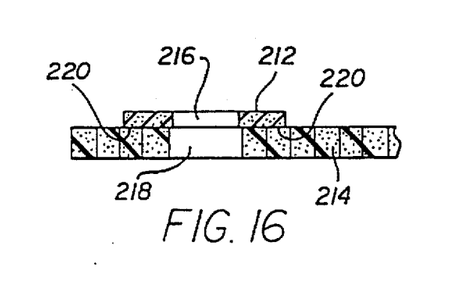
FIG. 16 is a sectional view of the support pad of FIG. 15 taken along line 16—16 of FIG. 15 showing that the additional pad has an aperture which is positioned over a pressure relief zone from which removable members have been removed.

FIG. 15 shows an additional pad 212 applied on top of resilient sections 214. Pad 212 has an aperture 216 to provide pressure relief to an ulcer. FIG. 16 shows that aperture 216 is positioned immediately adjacent to pressure relief zone 218, from which removable sections have been removed to create an area of low or no pressure. The bottom surface of additional pad 212 is provided with an adhesive layer 220 to attach the pad to the top surface of resilient sections 214. Any of a variety of commercial adhesives may be used, such as the 921 High Tech Adhesive manufactured by the 3M Company of St. Paul, Minn.

The additional pad may have any of a variety of sizes and shapes to accommodate a variety of different ulcer sizes and user weights. The pad may be made of a single-density material, or may have a multi-density layered arrangement consisting of a supple top layer for comfort and a dense lower layer to support body weight. The pad may also be cut into a grid pattern in order to reduce the shear forces on the foot during walking.

Furthermore, the user may choose to apply the additional pad to the plantar surface without removing any removable sections from the pad. For a particularly heavy user, leaving the removable sections in place provides padding beneath the injured area of the foot to further prevent the "bottoming out" that might otherwise occur as the user transfers weight to the injured area of the foot.

With regard to an alternative feature of the present invention, a problem called "window edema" occurs when an area of the body under low pressure is surrounded by an area of higher pressure. Body fluids tend to build up and become trapped in the area of lower pressure. Distal parts of the body, such as the hands and feet, are particularly prone to window edema because the cardio-vascular system typically does not do a good job of retrieving fluids that are far from the heart. The trapped fluids become excellent media for bacteria to grow, thereby causing infections.

Figure 17:
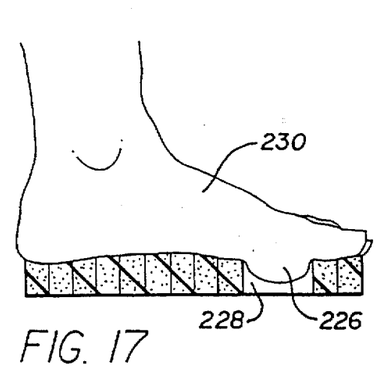
FIG. 17 is a side view of a support pad showing that fluids can become trapped in an injured area of the foot that is positioned over a pressure relief zone.

Window edema may be a problem for some users of the present invention. FIG. 17 show that fluids 226 may build up and become trapped in a pressure relief zone such as 228 under foot 230. Since foot 230 is far from the user's heart, the cardio-vascular system has trouble carrying away the fluids 226 that build up in relief zone 228. As bacteria grows in fluids 226, the user may be subject to a dangerous infection that can threaten the well-being of the foot.

Figure 18:
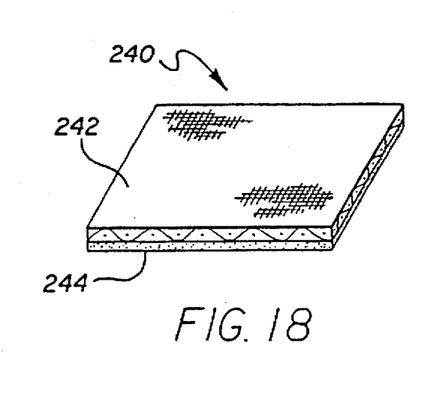
FIG. 18 is a perspective view of an edema patch having a stretch layer and an adhesive layer.

In order to prevent window edema in the present invention, an edema patch amy be provided in the relief area. FIG. 18 shows that an edema patch 240 may comprise a patch of stretch material 242 with an adhesive backing 244. Stretch material 242 may be the material sold under the trademark "LYCRA" or a similar material elastic properties. Adhesive 244 may be any of a variety of commercial adhesives, such as the 921 High Tech Adhesive manufactured by the 3M Company of St. Paul, Minn.

Figure 19:
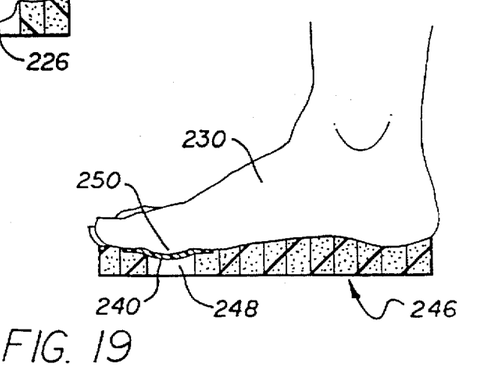
FIG. 19 is a side view of a support pad in which an edema patch has been applied over a relief zone area from which removable sections have been removed.
Figure 20:
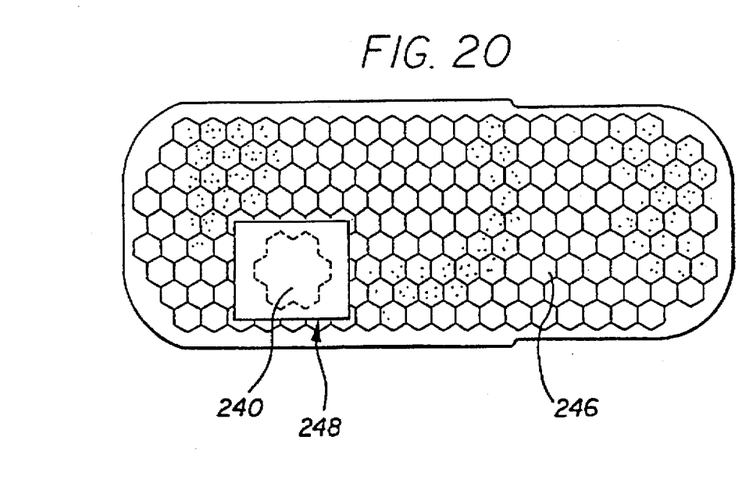
FIG. 20 is a top view of a support pad in which an edema patch has been applied over a relief zone area from which removable sections have been removed.

FIGS. 19 and 20 show an edema patch 240 applied to the plantar relief pad 246 to cover the opening of relief zone 248. The edema patch 240 adheres to a top surface of removable sections surrounding a relief zone from which a user has removed other sections, such that the edema patch covers the relief zone. Edema patch 240 applies some pressure to afflicted regions 250 of foot 230, thereby reducing the pressure difference between the afflicted area 250 and the area immediately surrounding relief zone 248. However, edema patch 240 generally applies less pressure to afflicted region 250 than would removable sections if inserted to fill relief zone 248. Nevertheless, edema patch 240 applies sufficient pressure to afflicted region of the foot 250 in order to reduce the likelihood of window edema.

The edema patch may be provided with a variety of features, and may be used in ways other than that shown in FIGS. 19 and 20. The patch may be of various sizes, shapes and stretch to accommodate particular sizes and shapes of afflicted areas. The patch may be applied to any area of the plantar pad where sections have been removed to create a pressure relief zone. If a user has created multiple pressure relief zones to accommodate multiple ulcers, the user may place an edema patch over each pressure relief zone.

Figure 21:
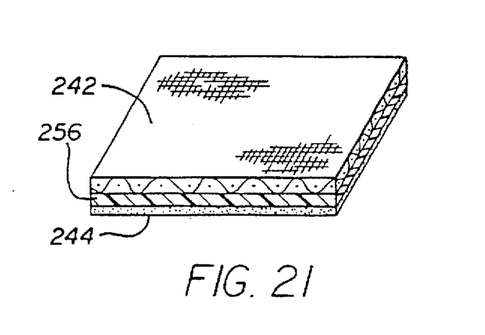
FIG. 21 is a perspective view of an edema patch having a layer of stretch material, a fluid-impermeable film, and an adhesive layer.

As FIG. 21 shows, the edema patch may further include a fluid-impermeable film layer 256 underlying the stretch material 242 in order to prevent fluid transmission from the foot into the area from which sections have been removed. Adhesive 244 is applied to the lower surface of film 256. Any of a variety of materials may be selected for the underlying film, including but not limited to urethane. The film thickness may be chosen to have substantial thickness, thereby limiting its stretchability and enabling it to give substantial support to the afflicted area of the foot. Alternatively, the film may have minimal thickness, which makes the film highly stretchable but limits the support that the film can give the foot.

Figure 22:
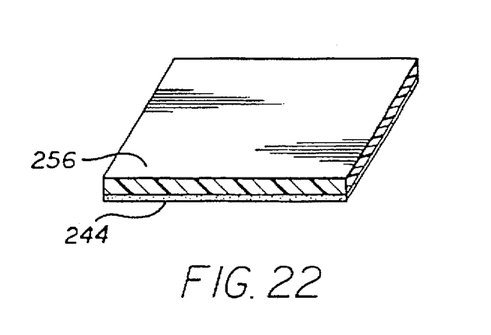
FIG. 22 is a perspective view of an edema patch having a fluid-impermeable film and an adhesive layer.

As an additional alternative, film 256 may overlie stretch material 242, with adhesive 244 being on the lower surface of stretch material 242. Film 256 and stretch material 242 may be bonded by pressing the film and stretch material together under high pressure. Alternatively, they may be bonded using any of a variety of commercial adhesives. Additionally, FIG. 22 shows that the patch may comprise a film layer 256 with adhesive layer 244 without any stretch material at all.

Figure 23:
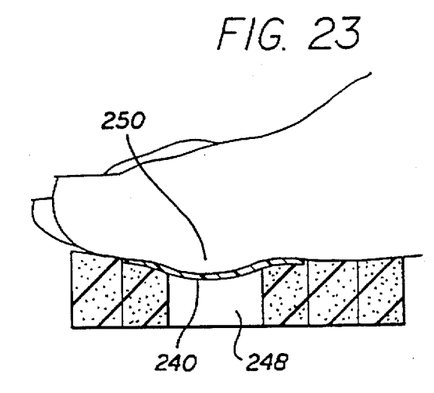
FIG. 23 is a side view of a support pad having an edema patch covering a pressure relief zone with the edema patch rounding the top edges of the pressure relief zone.

The edema patch provides another benefit to the user. The relief zone has edges that provide a "window" around the afflicted area. The foot may be subject to increased pressure at these edges, which physicians must often scythe to prevent skin irritation. However, as FIG. 23 shows, when an edema patch 240 is applied to the plantar pad to cover the pressure relief zone, the pad covers and smooths the edges of relief zone 248. There is then no need for a physician to scythe the edges.

Figure 24:
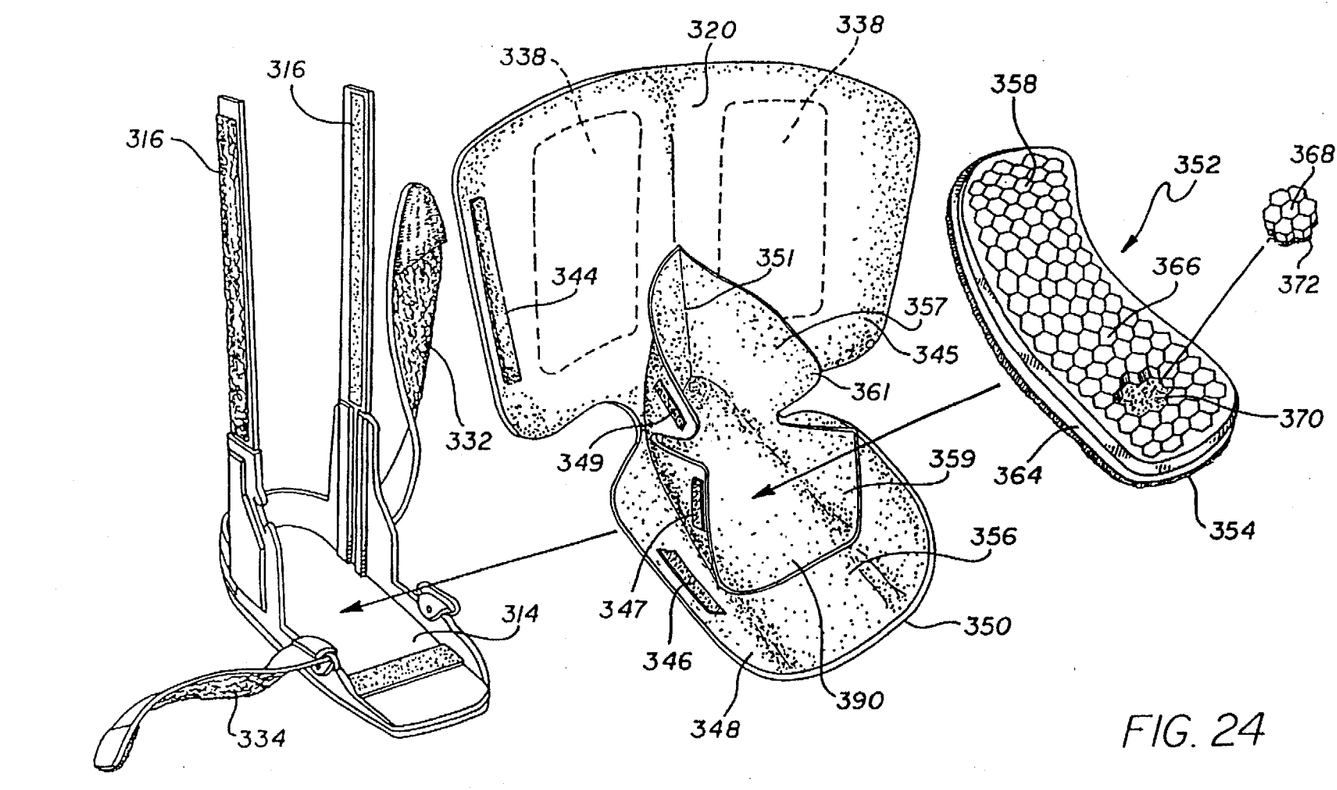
FIG. 24 is a partial exploded view of an alternative embodiment of a walker of the type to which the present invention applies.
Figure 25:
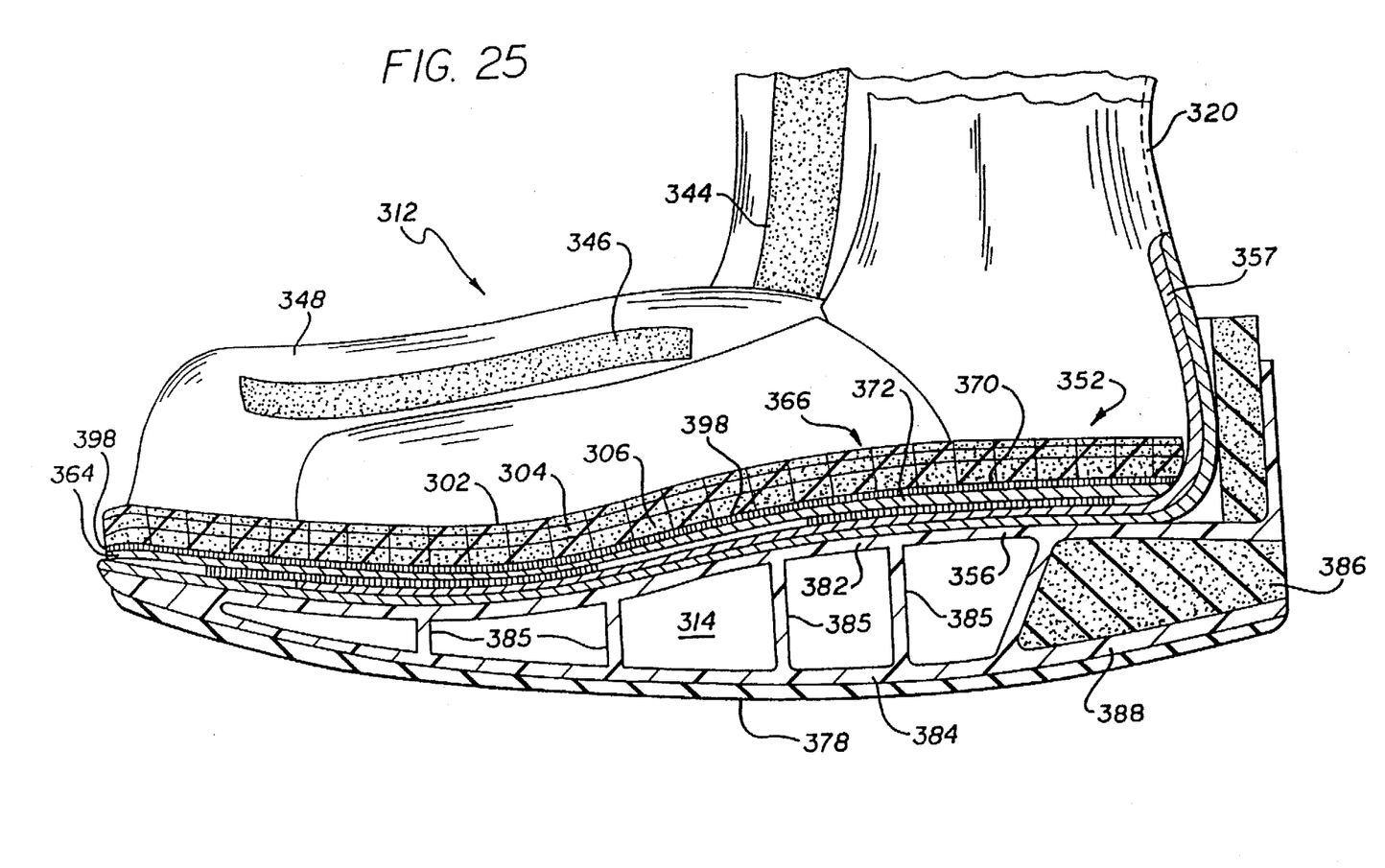
FIG. 25 is a partial cross-sectional view of the alternative embodiment of FIG. 24 taken along lines 3—3 of FIG. 1.

FIG. 24 and 25 illustrate an additional alternative embodiment of a walker that incorporates the present invention. FIG. 24 is a partial exploded view of an alternative embodiment of a walker of the type illustrated in FIG. 1. A feature of this embodiment is the inner booty 357, which holds the foot firmly in place within the walker.

FIG. 24 shows a walker including a frame made up of an outer sole assembly 314 and two side struts 316 secured to the sole, and extending up on either side of the lower leg of a patient. Within the frame 314, 316, is a soft goods type support member 320 for enclosing the lower leg, ankle and most of the foot of the patient or user. The soft goods member, which is of the type described previously in conjunction with FIG. 4, includes outer layers of cloth material separated by two layers of foam and bladders 338.

The soft goods body member 320 may be held in position within the frame 314, 316, by pads of hook and loop type material on the inner surface of the struts 316. Additionally, straps such as 28 of FIG. 1 may extend around the struts 316, through D-rings such as 30 in FIG. 1 and then fold back to be held in place by mating hook and loop areas on the surfaces of the straps. The straps 332 and 334 across the instep and the forward portion of the assembly, operate in similar manners to hold the foot and the soft goods type support member 320 in position within the frame 314, 316.

Elongated pad 344 is a strip of hook type material. As in the embodiment of FIG. 2, the outer cloth covering of the soft goods type body member 320 is of one of many well-known types cloth that will receive hook type securing pads such as that sold under the trademark "Velcro". The front upper portion of the soft goods type support member 320 may be held in the closed position by the engagement of the pad 344 with the outer surface of the mating portion 345 of the support member 320. Similarly, the pad 346 on the inner surface of the front flap 348 of the soft goods support member 320 serves to engage the mating flat 350 on its outer surface, and holds the front portion of the soft goods member around the upper portion of the patient's foot.

The present embodiment is provided with an inner booty 357 to provide additional means for retaining the foot within the walker. Inner booty 357 is sewn to soft goods body member 320 along seam 351. Elongated hook type pads 347 and 349 engage the inner surfaces of flaps 359 and 361, respectively, to adjustably hold the inner booty about the patient's ankle and foot.

The footgear of the present embodiment is provided with an inner sole assembly 352 which is preferably mounted within the soft goods support member 320 by a layer of hook type securing material 354 which is on the lower surface of the assembly 352, and which engages the inner surface of the soft goods type support member 320 in the area 356 and in the area 390 on inner booty 357.

Inner sole assembly 352 includes a lower cloth pad 364 and an upper resilient layer 366 constituting separate removable sections, also known as individually mobile resilient sections, which together form a normally substantially smooth surface for engagement by the foot. These sections are individually removable, as indicated by the sections 368 which are shown removed from the space 370 where they would normally be located to complete the smooth upper surface of the inner sole assembly 352.

Cloth pad 364 may be substantially indentation-free so that the resilient sections may be removed from any location on the grid. The user is thereby not limited to removing inserts only from indentations located in a limited number of positions on the sole. Instead, a user may remove sections from precisely the desired location.

The individual resilient sections such as the section 368, have hook or loop type securing material 372 on their lower surfaces, and the upper surface of the bladder 364 has mating hook and loop type material for removably securing sections such as section 368 in place to provide a relatively smooth upper surface. Thus, the group of sections 368 may be reinserted and re-secured into opening 370, and other sections removed, to accommodate different patient needs.

FIG. 25 is a somewhat schematic cross-sectional view of the present embodiment taken along line 3—3 of FIG. 1. Soft goods type support member 320 is shown here as a single layer for simplicity but which would actually be two layers of cloth and two foam layers forming a central foam core, as discussed in connection with FIG. 4. FIG. 25 also shows outer sole 314 including the lower tread portion 378, which would normally be somewhat rough for traction, the flap 348, the cloth pad 364, and the resilient inner sole 366. The sole 314 may include tread portion 378, and upper and lower high strength plastic sheet members 382 and 384 interconnected by appropriate ribs 385. Resilient foam material 386 controls flexing of the rear heel end 388 of lower plastic sheet member 384 provides increased cushioning for the patient.

Between the upper surface of cloth pad 364, and the lower surface of the inner sole 366 is a suitable material 398, for removably securing the inner sole 366 to the upper surface of the cloth pad 364. Material 398 may be hook and loop type material, or pressure sensitive adhesive, as noted hereinabove. The inner sole 366 may be formed of three layers 302, 304 and 306, which may be of progressively different softness and resiliency, with the softest and most resilient layer being the layer 302 closest to the foot, with layers 304 and 306 being progressively less resilient and providing somewhat greater support.

Another alternative embodiment of the present invention includes an inner sole having a plurality of independently vertically movable sections arranged in a grid pattern.

Figure 26:
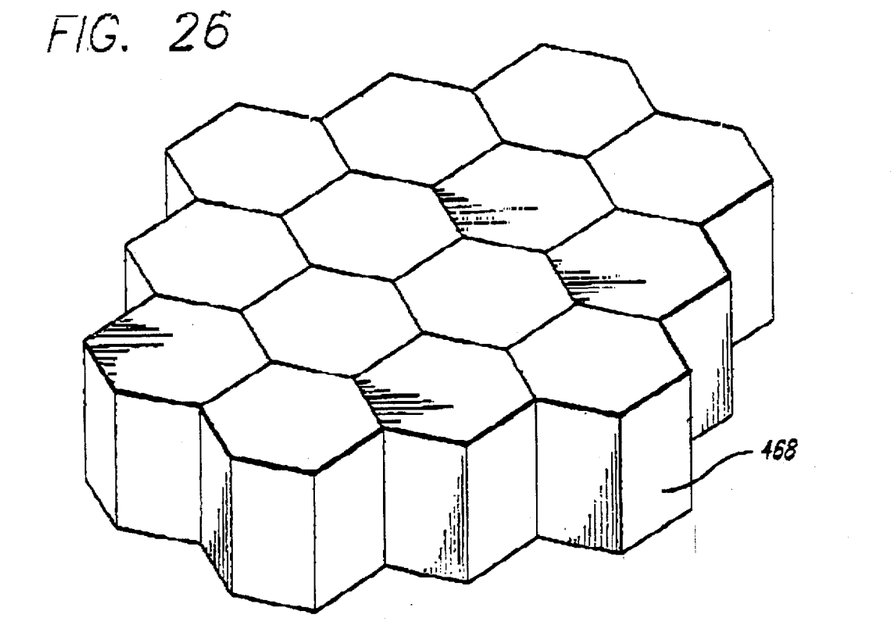
FIG. 26 is a perspective view of a pad having inflated pneumatic members.
Figure 27:
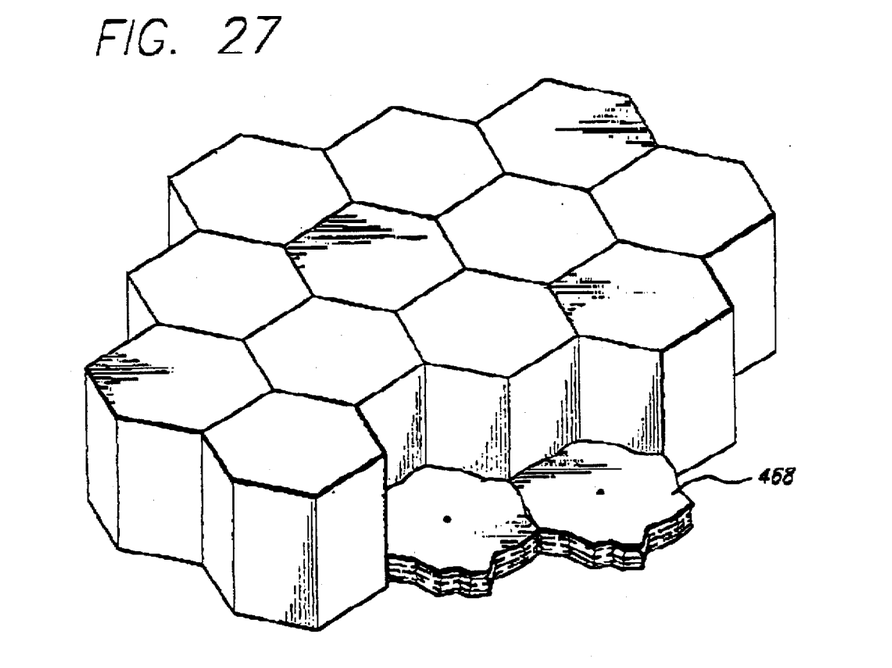
FIG. 27 is a perspective view of the pad of FIG. 26, with individual members having been deflated to provide pressure relief in a specific area of the pad.

Means are provided for independently and adjustably modifying the support of the foot at each section location. Referring to FIG. 26, the modifying means may include independent pneumtic sections 468 which a user may puncture to a partially or fully deflat, as illustrated in FIG. 27. The modifying means could alternatively include independent mechanical retention elements which a user would push down and which would then stay in place at a position below the surface of the sections that the user has not pushed down.

It should be noted that the various embodiments of the present invention provide means to reduce shear forces on the sole of the foot. The grid pattern of resilient sections creates a multiplicity of sections that sway laterally independently of one another in response to forces applied by the foot. Typical soles simply resist lateral foot motion, thereby inducing shear stresses on the bottom of the foot which may cause or aggravate ulcers. Thus, in contrast to typical soles, the grid pattern of independently mobile resilient sections of the present invention constitutes means for reducing shear stresses on the bottom of a foot as the user walks along.

It should also be noted that inner sole assembly 52 may be worn interchangeably with either the right or left foot. So, for instance, a user may use the inner sole assembly to pad the left foot for a time, then later use it to pad the right foot. Likewise, the entire walker 12 may be designed to be worn interchangeably on either the right or left leg.

Concerning the dimensions of the removable sections, one operative and presently preferred embodiment of the invention employs hexagonal removable elements of the type shown in FIG. 2, with the hexagons having a distance between opposing faces of approximately ½". Larger or smaller removable sections could be employed; however, it is preferred that the sections have a linear extent less than ¾". In the presently preferred embodiment, the removable sections are resilient and each have a height that is greater than its width and depth.

In conclusion, a number of illustrative embodiments of the invention have been discussed hereinabove. However, it is to be understood that various changes and modifications may be made without departing from the spirit and scope of the invention. Thus, by way of example and not of limitation, the air bladder under the sole may be embedded in the soft goods member or may be located under it, between the soft goods support member 20 and the outer sole assembly 14. In addition, the optional bladder may be filled with a variety of fluids other than air, such as gel or water. The invention is, of course, applicable to other types of footgear, in addition to walkers, for example, athletic shoes or normal walking shoes. Accordingly, the present invention is not limited to the precise embodiments described hereinabove.

What is claimed is:

1. A walker with pressure relief areas for the foot of a user, said walker having a sole area extending substantially for the entire area underlying the foot of a user, comprising:

a walker frame including an outer sole and struts extending from said sole upward;

a soft goods support for enclosing the ankle, lower leg and at least a portion of the foot, said support being secured to said frame;

an inner sole mounted in said soft good support, said inner sole including an underlying flexible sheet extending substantially over the entire sole area; and an upper resilient inner sole member extending over and being removably secured to said underlying flexible sheet, said upper resilient inner sole member having a substantially uniform thickness and extending substantially over the entire sole area;

said upper resilient inner sole portion being composed of a plurality of at least 50 separate resilient sections arranged in a grid pattern, said sections being removably secured on their lower surfaces to said underlying flexible sheet and said sections together forming a substantially smooth surface for engagement by the foot, said sections being individually removable to provide localized pressure relief to selected areas of the foot; and aid sections being directly adjacent one another to form said grid;

said grid pattern extending over substantially all of said upper inner sole member;

whereby one or a plurality of said sections may be removed at any desired area of the inner sole member to provide a relief zone corresponding to an afflicted zone of a foot.

2. A walker with pressure relief areas for the foot of a user, as defined in claim 1 wherein said upper resilient sole member includes at least 80 separate resilient sections.

3. A walker as defined in claim 1 wherein the inner sole portion has a central longitudinal axis, and wherein the inner sole portion is substantially symmetrical about said axis so that the walker may be used for either the left or the right foot and ankle of the user.

4. A walker as defined in claim 1 wherein said resilient sections are removably secured to said flexible sheet by hook and loop material; whereby said resilient sections may be easily removed and replaced.

5. A walker as defined in claim 4 wherein some of said separate resilient sections are taller than other of said sections so that a user may arrange said taller sections to custom fit a foot.

6. A walker as defined in claim 1 wherein said underlying flexible sheet is substantially indentation-free.

7. A walker as defined in claim 1 wherein some of said separate resilient sections are lower density sections and some are higher density sections so that a user may arrange said higher density sections to create at least one zone of additional support for a foot.

8. A walker as defined in claim 1 wherein said walker further comprises an additional resilient pad having an aperture and an adhesively-backed lower surface for attaching said additional pad to the upper surface of a plurality of said removable sections, said additional pad providing a region of additional support for a foot.

9. A walker as defined in claim 1 wherein said walker further includes an edema patch comprising a patch of stretch material having an adhesive layer on a lower surface thereof for adhering the edema patch to a top surface of removable sections surrounding a relief zone from which a user has removed other sections, such that the edema patch covers the relief zone.

10. A walker as defined in claim 9 wherein said edema patch further includes a fluid-impermeable film layer overlying said stretch material for preventing transmission of fluids through said edema patch.

11. A walker as defined in claim 1 wherein said walker further includes an edema patch comprising a patch of fluid-impermeable film having an adhesive layer on a lower surface thereof for adhering the edema patch to a top surface of sections surrounding a relief zone from which a user has removed other sections, such that the edema patch covers the relief zone.

12. A walker as defined in claim 11 wherein said edema patch further includes a layer of stretch material overlying said film patch.

13. A walker as defined in claim 1 wherein said separate resilient sections are hexagonal.

14. A walker as defined in claim 1 wherein said inner sole includes a plurality of layers, with the layer closest to the foot being substantially softer and more resilient than other layers.

15. A walker as defined in claim 1 further comprising means connected to said support for extending around the instep to hold the foot back into said support and in engagement with said inner sole.

16. A walker as defined in claim 1 wherein said inner sole extends to the rear beyond the heel of a patient and upward along and to the rear of the foot of the user.

17. A walker as defined in claim 1 wherein hook and loop type fabric holds the support to the walker frame.

18. A walker as defined in claim 1 wherein said walker further comprises a bladder for containing air which is mounted in said walker above said outer sole, and wherein said inner sole is mounted above said bladder.

19. Footgear with pressure relief areas for the foot, said footgear having a sole area extending substantially for the entire area underlying the foot of a user comprising:

an outer sole;

an inner sole extending substantially over the entire sole area mounted in said footgear above said outer sole, said inner sole having a plurality of independently vertically movable sections arranged in a grid pattern, said independently vertically movable sections having lower surfaces which are mounted within said footgear and said sections together form a substantially smooth surface for engagement by the foot;

means for independently modifying support of the foot provided at each section location;

said resilient sections being directly adjacent one another to form said grid; and said grid of resilient sections comprising substantially all of said inner sole and extending over substantially all of said sole area;

wherein said resilient sections have a height, a width and a depth, said height being greater than said width and depth.

20. Footgear as defined in claim 19 wherein said means for independently modifying the support of the foot comprises independent mechanical retention elements.

21. Footgear with pressure relief areas for the foot, comprising:

an outer sole;

an inner sole mounted in said footgear above said outer sole, said inner having a plurality of independently vertically movable sections arranged in a grid pattern, said independently vertically movable sections having lower surfaces which are mounted within said footgear and together form a substantially smooth surface for engagement by the foot;

means for independently modifying the support of the foot provided at each section location;

said resilient sections being directly adjacent one another to form said grid; and said grid of resilient sections comprising substantially all of said inner sole;

wherein said resilient sections have a height, a width and a depth, said height being greater than said width and depth; and said means for independently modifying the support of the foot comprising independent pneumatic sections which a user may puncture to deflate.

22. Footgear with pressure relief areas for the foot, said footgear having a sole area extending substantially for the entire area underlying the foot of a user, comprising:

an outer sole, an inner sole extending substantially over the entire sole area mounted in said footgear above said outer sole, said inner sole having a plurality of removable sections that are removable mounted in said footgear and that are arranged in a grid pattern said removable sections having lower surfaces which are removable secured within said footgear and said sections together forming a substantially smooth surface for engagement by the foot said sections being individually removable from said footgear to provide localized relief to selected areas of the foot;

said resilient sections being directly adjacent to one another to form said grid, with substantially no space in between said sections except when at least one of said sections has been removed; and said grid of resilient sections comprising substantially all of said inner sole and extending substantially over the entire sole area;

wherein said footgear further comprises a bladder for containing fluid, mounted in said footgear above said outer sole, and said removable sections are mounted in said footgear above said bladder.

23. Footgear with pressure relief zones for the foot, said footgear having a sole area extending substantially for the entire area underlying the foot of a user, comprising:

an outer sole;

an inner sole extending substantially over the entire sole area mounted in said footgear above said outer sole, said inner sole having a plurality of separate individually mobile resilient sections arranged in a grid pattern, said sections being removable secured on each of their lower surfaces to an underlying flexible sheet such that a user may disengage a lower surface of one or more of said sections from said flexible sheet for removal from said footgear, said resilient sections forming a surface for engagement by a foot;

said resilient sections being directly adjacent one another to form said grid and extending over substantially all of said sole area; and an edema patch for covering an open space left after a user has removed at least one mobile section from said grid, said edema patch comprising an upper patch body having a lower surface and an adhesive layer on said lower surface for adhering said patch to mobile resilient sections surrounding the open space;

wherein said footgear further comprises a bladder for containing fluid, mounted in said footgear above said outer sole, and said resilient sections are mounted in said footgear above said bladder;

whereby one or a plurality of said adjacent sections may be removed at any desired area of the inner sole to provide relief corresponding to an afflicted zone of the foot, said edema patch being placed over the removed sections to apply pressure to the afflicted zone of the foot, thereby preventing fluids from building up therein.

* * * * *